United States Patent [19]

Terwilliger et al.

[11] Patent Number: 4,940,061
[45] Date of Patent: Jul. 10, 1990

[54] BIOPSY INSTRUMENT

[75] Inventors: Richard A. Terwilliger, Alamo; Daniell Hebert, San Francisco; Jack Hall, Portola Valley, all of Calif.

[73] Assignee: Ingress Technologies, Inc., Phoenix, Ariz.

[21] Appl. No.: 441,776

[22] Filed: Nov. 27, 1989

[51] Int. Cl.$^5$ .............................................. A61B 10/00
[52] U.S. Cl. .................................... 128/754; 606/171
[58] Field of Search ............... 128/749, 751, 754, 755, 128/305; 606/167, 170, 171

[56] References Cited

U.S. PATENT DOCUMENTS

| 2,710,000 | 6/1955 | Cromer et al. | 128/2 |
|---|---|---|---|
| 3,452,741 | 7/1969 | Schaffer | 128/2 |
| 3,613,662 | 10/1971 | Chrysostomides | 128/2 B |
| 4,210,146 | 7/1980 | Banko | 128/305 |
| 4,461,305 | 7/1984 | Cibley | 128/754 |
| 4,589,414 | 5/1986 | Yoshida et al. | 128/305 |
| 4,600,014 | 7/1986 | Beraha | 128/754 |
| 4,699,154 | 10/1987 | Lindgren | 128/754 |
| 4,706,669 | 1/1987 | Schlegel | 128/329 R |

FOREIGN PATENT DOCUMENTS 8303343 10/1983 PCT Int'l Appl. ................. 128/754

OTHER PUBLICATIONS

Publication fr. Amedic AB, Märsta, Sweden, titled, "The Needle Guide".

Primary Examiner—Randall L. Green
Assistant Examiner—Randy Shay
Attorney, Agent, or Firm—Charles E. Cates; Richard G. Harrer

[57] ABSTRACT

An instrument for removing tissue samples from a tissue mass which automatically penetrates, severs, and removes a tissue portion for examination. The instrument is motor powered, preferably by self-contained rechargeable batteries, and employs electrically actuated stops to control the action of penetration into and retraction from the tissue mass. The tissue penetrating means and severing means includes an inner stylet which penetrates the tissue mass and a hollow outer tube or cannula which surrounds the stylet and serves to sever a sample of tissue. In a preferred form the tissue penetrating end of the stylet is notched so that when the stylet penetrates the tissue mass, a portion of the tissue relaxes in the notched area. After tissue penetration by the stylet, the cannula, having a cutting surface at its distal end, penetrates the tissue and cuts off the tissue portion residing in the notched area of the stylet. The tissue penetrating and severing means are operably connected to a motor powered rotary cam assembly by means of cam followers and the rotary motion of the cam is converted to sequential, linear motion in the tissue penetrating means and severing means, the linear motion being of substantially constant force and velocity.

20 Claims, 6 Drawing Sheets

BIOPSY INSTRUMENT

FIELD OF THE INVENTION

This invention relates to an instrument for extracting samples of tissue from humans and other animals and more particularly to an instrument for automatically performing a biopsy of a tissue mass in an accurate, expeditious manner with a minimum of discomfort to the patient.

BACKGROUND OF THE INVENTION

It is often desirable and frequently absolutely necessary to sample or test a portion of tissue from humans and even other animals, particularly in the diagnosis and treatment of patients with cancerous tumors, pre-malignant conditions and other diseases or disorders. Typically in the case of cancer, when the physician establishes by means of procedures such as palpitation, x-ray or ultra sound imaging that suspicious circumstances exist, a very important process is to establish whether the cells are cancerous by doing a biopsy. Biopsy may be done by an open or closed technique. Open biopsy removes the entire mass (excision biopsy) or a part of the mass (incision biopsy). Closed biopsy on the other hand is usually done with a needle-like instrument and may be either an aspiration or a core biopsy. In needle aspiration biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section.

The type of biopsy depends in large part in circumstances present with respect to the patient and no single procedure is ideal for all cases. However, core biopsy is extremely useful in a number of conditions and is being used more frequently by the medical profession.

A variety of biopsy needles and devices have been described and used for obtaining specimens of tissue. For example, reference is made to U.S. Pat. Nos. 4,651,752; 4,702,260; and 4,243,048 which show biopsy needles of varying types. Additionally, a number of very specialized devices for extracting samples of tissue have been described such as the biopsy device in U.S. Pat. No. 4,461,305, which device is designed specifically for removing a sample of tissue from the female uterine cervix. Other devices have been disclosed which relate to surgical cutting instruments. For example, U.S. Pat. No. 4,589,414 discloses an instrument which is particularly designed to operate in the area of the knee to withdraw tissue chips. Also available are so-called biopsy guns for removing a core of tissue which customarily are spring powered devices and must be cocked with considerable force. When actuated such guns produce a loud snapping noise, combined with a jerking action. Such a biopsy gun may employ a needle set consisting of an inner stylet and an outer tube called a cannula. The stylet is a needle like device with a notched cut-out at its distal end. The cannula in effect is a hollow needle with an angled cutting surface at its distal end which slides over the stylet. When the stylet is forced into tissue, the tissue is pierced and relaxes into the notched cut-out of the stylet. When the cannula is then slid forward, the tissue in the notch of the stylet is sliced off and retained in the notch until the cannula is withdrawn. Examples of such devices are shown in U.S. Pat. Nos. 4,600,014 and 4,699,154. Although such spring powered biopsy guns will remove a core or sample of tissue, they have rather serious disadvantages. For one, they must be manually cocked with a plunger bar. Such "cocking" of the gun requires considerable force and the gun must be cocked for each biopsy cut. A further disadvantage is that the springs provided in the gun accelerate the needles until a mechanical stop position is reached, creating a loud snapping noise and jerking motion which is a problem both to the physician and the patient. This noise and jerking action can cause the patient to jump and in some cases even prevents the physician from striking the intended tissue target. Another disadvantage is that the force and velocity delivered to the stylet and cannula rapidly diminishes when traveling from a retracted to a fully extended position resulting in tissue samples of lower quality.

Accordingly it is a principal object of this invention to provide an instrument for obtaining samples of tissue from tissue masses;

It is a further object of this invention to provide a biopsy instrument which is able to provide a substantially constant force and velocity to that portion of the instrument which penetrates the tissue mass and severs a portion of tissue for further examination.

It is another object of this invention to provide an instrument for automatically performing a biopsy of a tissue mass in an accurate and expeditious manner with a maximum of accuracy and a minimum amount of discomfort to the patient;

It is a still further object of this invention to provide a instrument for performing tissue mass biopsies by removing a core or sample of tissue, which instrument eliminates the need for springs and mechanical stops, which is silent in operation and has the ability to effectively penetrate even small tissue masses.

It is another object of this invention to provide an instrument for obtaining tissue samples from tissue masses which instrument requires no manual setting or cocking and which may be "fired" multiple times without any abrupt starts or stops.

It is still another object of this invention to provide a biopsy instrument which includes means to convert rotary motion to sequential, linear motion of substantially constant force and velocity to the means for penetrating and severing a tissue sample from a tissue mass.

These and other objects of the invention will be apparent from the following description and claims.

STATEMENT OF THE INVENTION

Based on the prior art instruments for biopsy samples from tissue masses, and the actual present state of this art, there then exists a need for an instrument which is capable of automatically removing a tissue sample or core sample of pre-determined size where the process is done very rapidly, is easily repeated if required, is accurate, is relatively simple for the physician to use, is virtually noiseless, and in use results in minimal discomfort to the patient.

Accordingly, we have invented an instrument for removing tissue samples from a tissue mass which instrument automatically penetrates, severs, and removes the tissue portion for examination. The instrument is motor powered, preferably by self-contained rechargeable batteries, and employs electrically actuated stops instead of mechanical stops to control the action of penetration and retraction from the tissue mass. The portion of the instrument which penetrates the tissue mass and severs a portion thereof, the tissue penetrating and severing means, includes an inner stylet which penetrates the tissue mass and a hollow outer tube or cannula which surrounds the stylet and serves to sever a sample of tissue. In a preferred form the tissue penetrating end of the stylet is notched so that when the stylet penetrates the tissue mass, a portion of the tissue relaxes in the notched area. After tissue penetration by the stylet, the cannula, having a cutting surface at its distal end, penetrates the tissue and cuts off the tissue portion residing in the notched area of the stylet. The tissue penetrating and severing means are operably connected to a special motor powered rotary cam assembly by means of cam followers and it is a feature of this invention that the rotary motion of the cam is converted to sequential, linear motion in the tissue penetrating and severing means, the linear motion being of substantially constant force and velocity.

In operation, the physician or technician actuates the instrument by pressing a button causing the stylet to move forward in a rapid, precise manner and penetrate the tissue mass followed with penetration of the mass by the cannula, resulting in a portion or core of tissue being severed and retained in the notched portion of the stylet. Further actuation by the physician causes the cannula to retract exposing the tissue sample in the stylet for easy removal. An additional actuation causes retraction of the stylet and a resetting of the cannula/stylet assembly for further use.

In a preferred embodiment, the instrument has two actuators or buttons which cycle the action of the stylet/cannula assembly as described above. Actuation of one button, called a fire button, causes penetration of the stylet and cannula into the tissue mass. An initial actuation of the other button, called a retract button, causes retraction of the cannula to expose a sample of the tissue. A second actuation of the retract button retracts the stylet and the instrument is ready for further use.

Special electrical circuitry allows the stylet/cannula assembly to move in a forward or reverse direction via the rotary motion of a special function cam assembly with a cam travel of approximately 360 degrees. Motion within a single revolution of the cam is controlled via a limit switch assembly, stopping the motion at predefined stylet/cannula assembly locations of, for example: (1) where both the stylet and cannula are forward; (2) where the stylet is forward but the cannula has been moved back; and (3) where both the stylet and cannula are back. The limit switch assembly includes two principal components, a stationary limit switch wiper plate and a rotary limit switch board. The stationary limit switch wiper is provided with spring finger contacts which are electrically connected to the actuation buttons and other circuit components. The rotary limit switch board is a circuit board which is fixed to a rotatable drive shaft and rotates therewith. An electrically conductive circuit pattern is present on one face and the wiper plate and rotary limit switch board are mounted in line in the instrument and in contact with each other concentrically about the drive shaft. As the drive shaft rotates either clockwise or counterclockwise, the circuit pattern on the rotary limit switch board creates particular circuit paths by contacting specific spring finger contacts on the stationary limit switch plate during the rotational motion. The purpose of these specific circuit paths on the rotary limit switch board allows the stylet/cannula assembly to stop at prescribed positions.

The instrument is also provided with what is called a toggle assembly which includes a stationary wiper plate, a toggle board and a toggle plate. The stationary wiper plate is similar to the stationary limit switch wiper plate in the limit switch assembly and is provided with spring finger contacts which are electrically connected to the actuation buttons and other circuit components. The toggle board has an electrically conductive circuit pattern present on one face. The wiper plate and toggle board are mounted in line and in contact with each other concentrically about the drive shaft. As the drive shaft rotates either clockwise or counterclockwise, a key on the drive shaft encounters a protrusion in the central opening of the toggle board. When the key and the protrusion meet the toggle board is forced to rotate a slight distance in a clockwise or counterclockwise direction and the circuit pattern on the toggle board creates again a specific electrical circuit by contacting specific spring finger contacts on the stationary wiper plate. The purpose of the specific circuit paths of the toggle board is to allow the stylet/cannula assembly to travel in prescribed directions either forward or backward via depression of the retract button. This particular construction and circuitry allows the retract button to serve as a dual function switch in the retraction phase of the action of the biopsy instrument. Thus after the forward motion of the stylet/cannula assembly is completed, the retract button can be depressed and the stylet of the stylet/cannula assembly moves backward through approximately one-half a revolution of the special function cam. The limit switch assembly stops the motion at approximately the mid-point of reverse travel of the cam and the toggle board is again mechanically rotated either clockwise or counterclockwise as previously described. The shift in the position of the toggle board changes the electrical circuitry to allow a second actuation of the retract button which permits the continuation of the reverse motion until the limit switch assembly stops rotation of the cam and the cannula is fully retracted.

BRIEF DESCRIPTION OF THE DRAWINGS

The above noted advantages and other characteristic features of the present invention will be in part apparent from the accompanying drawings, and in part pointed out in the following detailed description of the preferred embodiment of the invention in which reference will be made to the accompanying drawings wherein like reference numerals designate corresponding parts and wherein:

FIG. 13 is a section taken on the line 13—13 of FIG. 11A.

DESCRIPTION OF A PREFERRED EMBODIMENT

Figures 1, 5:
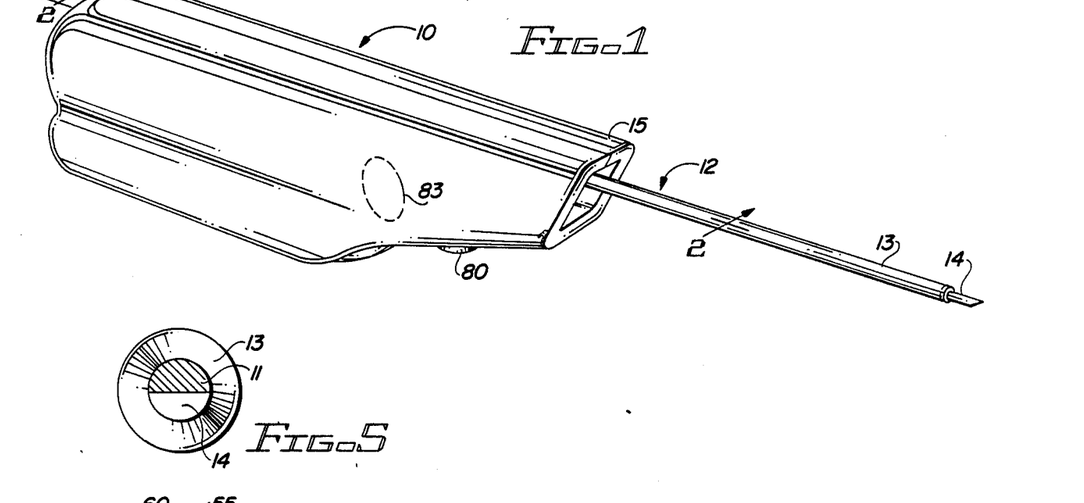
FIG. 1 is a perspective view of the biopsy instrument of this invention.
FIG. 5 is a cross section of the stylet/cannula assembly taken on the line 5—5 of FIG. 4D.
Figure 2:
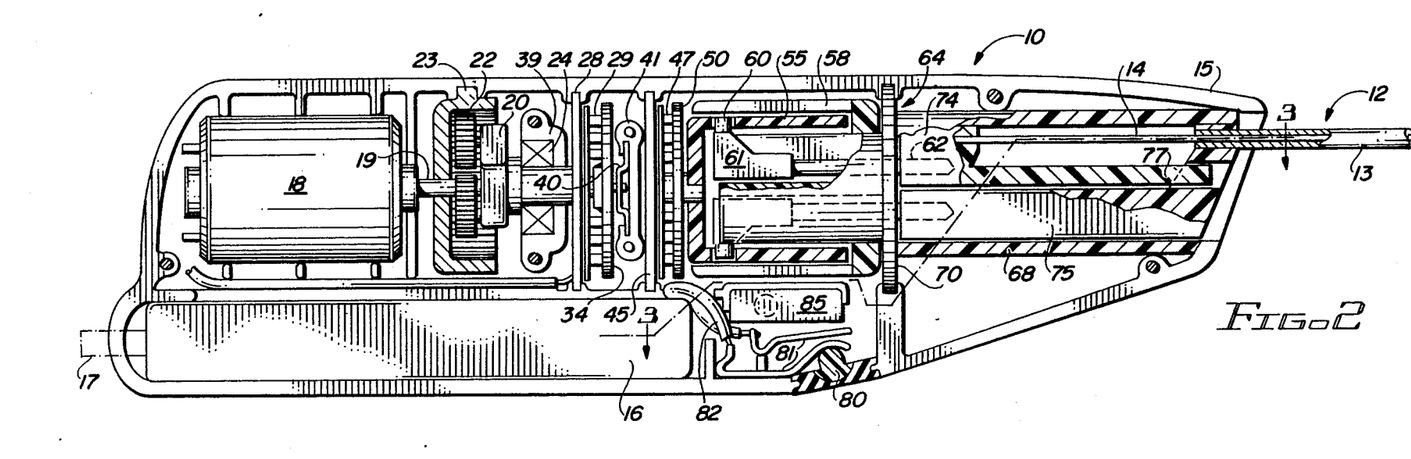
FIG. 2 is a side elevational view taken on the line 2—2 of FIG. 1.

Considering now the drawings in detail, FIG. 1 illustrates a perspective view of one embodiment of the inventive biopsy instrument which is shown generally at 10 with the tissue piercing and removing means shown generally at 12. The tissue piercing and removing means comprises a stylet 14 and cannula 13. Referring to FIG. 2 which is a sectional view through the instrument shown in FIG. 1, and FIG. 6, which is an exploded view of a number of the components of the instrument, the instrument 10 is shown as having an outer housing 15 provided with a motor 18 mounted in one end thereof. Motor 18 is reversible and preferably of the DC type and preferably powered by rechargeable batteries 16 contained within the housing. Suitable contacts 17 are provided to recharge the batteries. Motor 18 is operably engaged with planetary gear assembly 20 by means of shaft 19 which shaft engages central gear 21. Central gear 21 in turn meshes with planetary gears 22 which in turn engage with annulus gear 23. In a preferred embodiment the DC motor operates at about 10,000 rpm with the gearing being about a 6:1 ratio. One end of the planetary gear set 20 is mounted in bearing 24 which in turn is secured within the housing by bracket 39. Drive shaft 25 is secured at its end 26 in the D-shaped opening 35 of the planetary gear set by means of a set screw or other suitable fastening means.

Figures 6, 6A, 6B, 7:
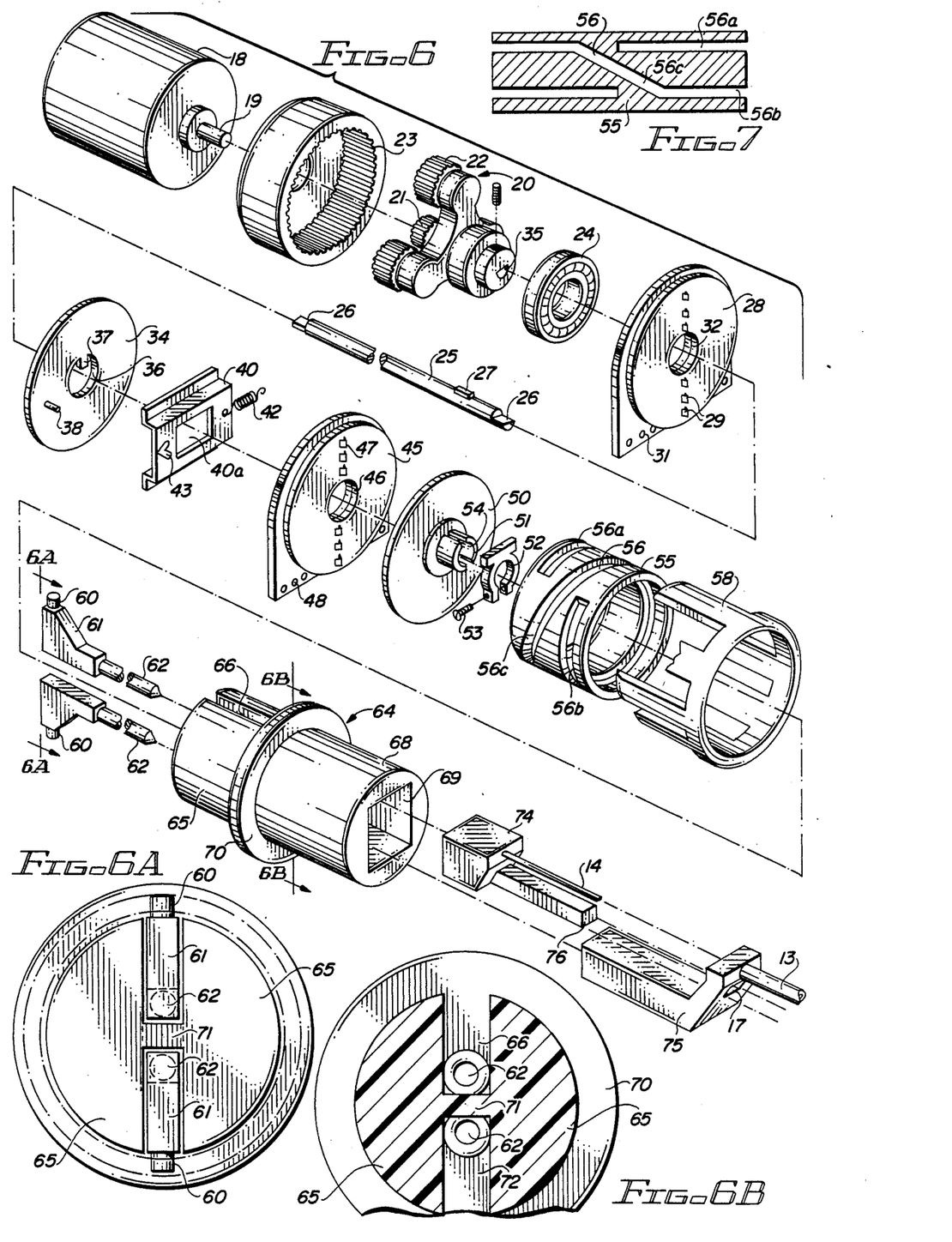
FIG. 6 is an exploded perspective view of the biopsy instrument illustrating the major component parts thereof.
FIGS. 6A and 6B are sectional views of the instrument taken on the lines 6A—6A and 6B—6B respectively of FIG. 6.
FIG. 7 is a plan view of the rotary cam showing the cam grooves.
Figure 8:
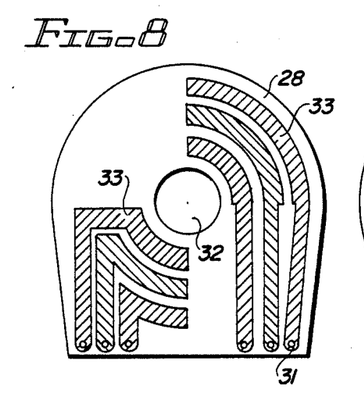
FIG. 8 is an elevational view of one side of the wiper assembly.
Figure 9A:
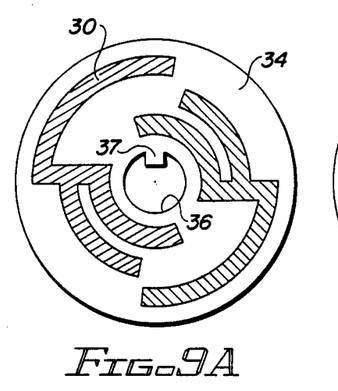
FIG. 9A is an elevational view of one side of the toggle printed circuit board.

Positioned adjacent to the gear assembly are the means for controlling the movement of the stylet/cannula assembly 12 in a forward (piercing) direction or in a reverse direction with respect to the tissue mass. Such means includes a toggle assembly comprising stationary wiper plate 28, a toggle board 34 and a toggle plate 40. Positioned adjacent to the toggle assembly is a limit switch assembly comprising a limit switch wiper plate 45 and a limit switch board 50, all as best shown in FIG. 6. Stationary wiper plate 28 is provided with a central opening 32 for passage of drive shaft 25. On one side of wiper plate 28 is a series of vertically positioned contact pins 29. Along the base of the wiper plate are a series of wire contact posts 31. As shown there are six spring contact pins and six contact posts. As shown in FIG. 8, the reverse side of stationary wiper plate 28 is provided with a series of electrically conductive circuit paths 33 with one end of each circuit path connected to a wire contact post 31 and the other end connected to a contact pin 29. Immediately adjacent to the stationary wiper plate 28 is circular shaped toggle board 34 having a central opening 36 for passage of drive shaft 25 with a protrusion 37. Positioned toward the outer edge of toggle circuit board 34 and on one side thereof is pin 38. As shown in FIG. 9A, the reverse side of the toggle circuit board 34 is provided with a series of electrically conductive circuit paths 30. Certain of the spring contact pins 29 make contact with circuit paths 30.

The toggle assembly is completed by the toggle plate 40 mounted and positioned within the instrument by bracket 41. Again as shown in FIG. 6, the toggle plate is provided with a central rectangular opening 40a, V-shaped opening 43 and spring 42 which is secured to an inner wall of housing 15. In the assembled instrument, pin 38 of toggle board 34 rides within V-shaped opening 43 and this combination serves to control the amount of rotary movement of the toggle board. The toggle board can rotate a distance in either a clockwise or counterclockwise direction and the amount of rotation is controlled by pin 38 in V-groove 43.

Figure 9B:
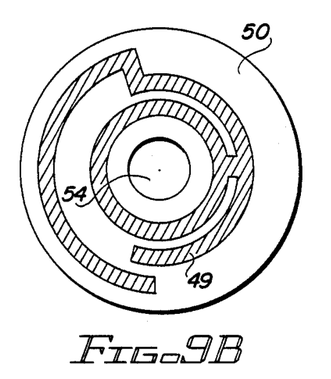
FIG. 9B is an elevational view of one side of the wiper assembly of the limit switch assembly.

Adjacent to the toggle assembly is the limit switch assembly made up of stationary limit switch wiper plate 45 and limit switch board 50. Wiper plate 45 is similar in construction to the stationary wiper plate 28 of the toggle assembly having a central opening 46 and being provided on one side thereof with a series of vertically positioned contact pins 47 and a series of wire contact posts 48 along the base of the wiper plate 45. The contact pins 47 make direct contact with a side of the limit switch board 50 and this side of the limit switch board is shown in FIG. 9B. As with the stationary wiper plate 28 and the toggle board 34, board 50 has a central opening 54 and electrically conductive circuit paths 49. Limit switch board 50 rotates with drive shaft 25 and is therefore provided with a split collar 51 for passage of the shaft 25. Clamp 52 surrounds the collar 51 and when tightened by screw 53 insures that the limit switch board will rotate with shaft 25.

The components of the instrument which guide the stylet/cannula assembly 12 will now be detailed. As previously described, the physician or technician actuates the instrument causing the stylet 14 to move forward in a rapid and precise manner to penetrate the tissue mass followed by penetration of the mass by the cannula 13, resulting in a portion or core of tissue being severed and retained in the notched portion of the stylet. Further actuation causes the cannula to retract exposing the tissue sample in the notched portion at the distal end of the stylet for easy removal. An additional actuation causes retraction of the stylet and a resetting of the cannula/stylet assembly for further use. The penetration and retraction of the stylet and cannula assembly is controlled in part by hollow rotary cam 55 which is best illustrated in FIGS. 6 and 7. Cam 55 is provided with a continuous groove 56 and a preferred groove pattern is shown in even greater detail in FIG. 7. As shown, continuous groove 56 is made up of three sections. A first groove section 56a is positioned substantially parallel to one end of cam 55 and extends about a portion of the circumference of the cam. A second groove section 56b is positioned substantially parallel to the other end of the cam and also extends about a portion of the circumference of the cam. Section 56c connects section 56a and 56b in a generally diagonal manner. Cam 55 is rotated by means of drive shaft 25 and, as partly shown in FIGS. 4A-4D, this is accomplished by securing shaft end 26 into the opening 63 of the end wall 59 of cam 55. Thus rotation of shaft 25 in a clockwise or counterclockwise direction causes identical rotation of the cam. Housing 58 surrounds cam 55 and serves to properly position the cam within the instrument.

As previously described, stylet 14 moves within and is surrounded by cannula 13. The non-penetrating end of stylet 14 is mounted in stylet block 74. Correspondingly, the non-penetrating end of cannula 13 is mounted into cannula block 75. As shown in FIG. 6, stylet block 74 is provided with extension 76 which is in alignment with and moves through opening 77 of the cannula block 75 to aid in proper alignment of the stylet and cannula blocks and therefore the stylet/cannula assembly.

Mounted in the ends of each of the cannula and stylet blocks are drive rods 62 which rods are in turn secured to drive arms 61. Each of drive arms 61 is provided with cam follower 60, which ride in the continuous groove 56 of cam 55. Thus, rotation of cam 55 will result in sequential linear movement of the stylet and cannula.

Figure 4A:
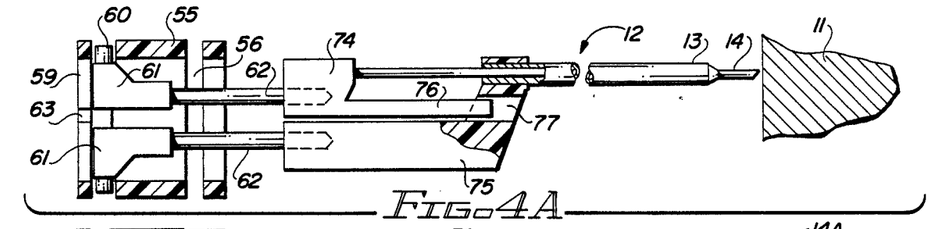
FIGS. 4A–4D are part side elevational views showing the action involved in penetration of a tissue mass by the stylet and cannula and retraction of the cannula from the tissue mass.
Figure 4B:
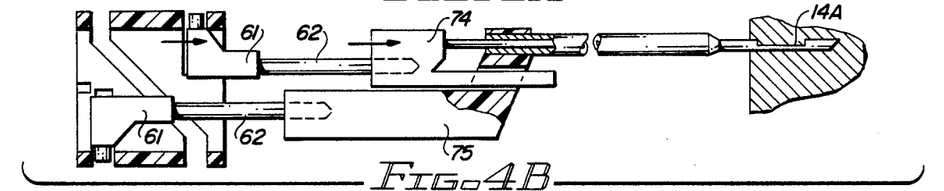
Figure 4C:
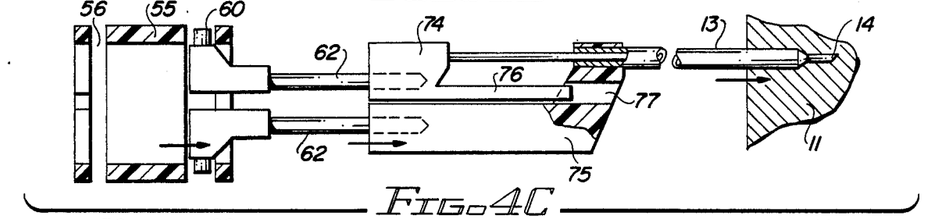
Figure 4D:
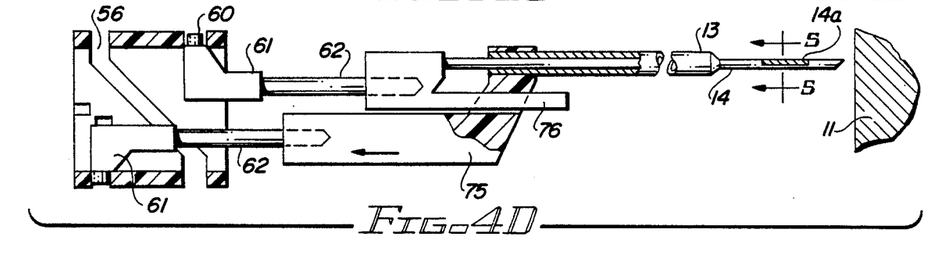

This sequential linear movement is well illustrated in FIGS. 4A-4D. In FIG. 4A, each of the stylet 14 and cannula 13 are in a retracted position and immediately adjacent the tissue mass 11. Initial rotation of cam 55, as shown in FIG. 4B, results in lateral movement of stylet block 74 and its attached stylet to penetrate the tissue mass where a portion of the tissue is caught in notch 14a. Continued rotation of the cam, as shown in FIG. 4C, results in movement of the cannula block 75 and its attached cannula into the tissue mass severing the portion of the tissue within notch 14 from the tissue mass. As shown in FIG. 4D, rotation of cam 55 has been reversed thus causing retraction of the cannula exposing the tissue sample in notch 14a for easy removal by the technician. Further rotation of cam 55 will result in retraction of the stylet and the instrument is again ready for use as shown in FIG. 4A.

Because of the need for precise movement of stylet and cannula, guide means shown generally at 64 are used to further aid in proper alignment of the stylet/cannula assembly. As shown in FIGS. 6, 6A and 6B, guide means 64 includes a generally cylindrical shaped housing 68 having a rectangular opening 69 approximately sized to accommodate the stylet and cannula blocks 74 and 75. Thus the stylet and cannula blocks move laterally within the interior of housing 68 and bear on the interior walls of the housing aiding proper alignment. In addition, guide means 64 also includes a cylindrical shaped guide 65 and bulkhead 70, the latter separating guide 65 and housing 68. Guide 65, as best shown in FIG. 6B, is a solid cylinder provided with vertical channels 66 through which drive rods 62 operate. Guide 65 is so constructed that separator 71 is provided between channels 66 to assist in maintaining proper spacing and alignment of the drive rods.

In a preferred embodiment, the instrument has two actuators or buttons which set as to motion the action of the stylet/cannula assembly. Actuation of the fire button, causes initial penetration of the stylet into the tissue mass followed by penetration of the cannula. The initial actuation of the retract button, causes retraction of the cannula exposing the sample of tissue. A second actuation of the retract button retracts the stylet and the instrument is ready for further use.

Figure 3:
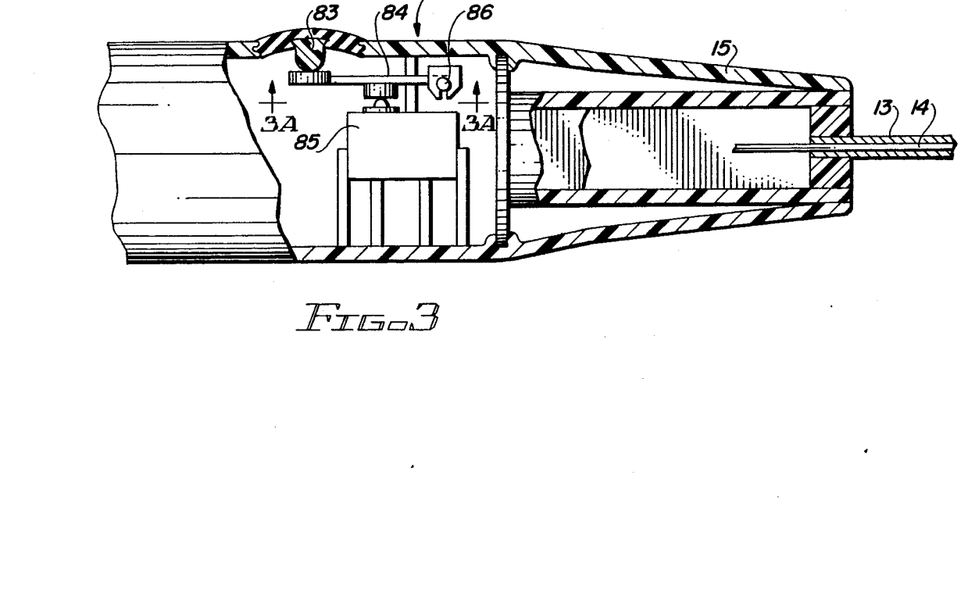
FIG. 3 is a part side elevational view taken on the line 3—3 of FIG. 2.
Figure 3A:
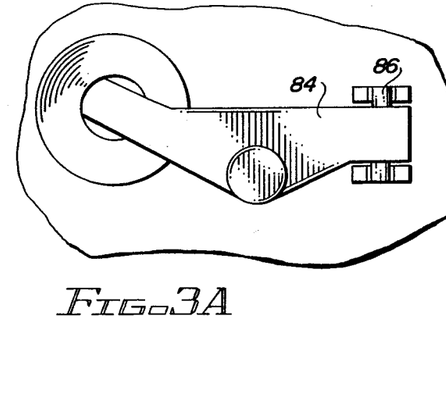
FIG. 3A is a side elevational view taken on the line 3A of FIG. 3.

Thus, as shown in FIGS. 2, 3 and 3A, the instrument includes retract button 80 and a fire button 83, both of which are preferably provided with a rubber seal. As shown in FIG. 2, the retract button is located on the underside of the instrument. Depression of the retract button engages contacts 81 completing the circuit and allowing current to flow into wire 82. As illustrated in FIG. 3, fire button 83 is located away from the retract button and on one side of the instrument. The depression of fire button 83 actuates micro switch 85 by means of lever 84 mounted on pivot pin 86.

The biopsy instrument is provided with an assembly and circuitry which permits the stylet/cannula assembly to move in a forward or reverse direction via the rotary motion of the special function cam assembly with a rotation of approximately 360 degrees. Rotation of cam 55 is controlled via the limit switch assembly, stopping the rotation at pre-defined stylet/cannula assembly locations of, for example: (1) both the stylet/cannula are forward; (2) the stylet is forward but the cannula has been moved back; and (3) where both the stylet and cannula are back. Such limit switch assembly is composed of two principal components, stationary limit switch wiper plate 45 and rotatable limit switch board 50. Stationary wiper plate 45 is provided with six spring finger contacts 47 which are electrically connected to the actuation buttons 80 and 83 and other circuit components. The limit switch board 50 is a circuit board which is fixed to the drive shaft 25. An electrically conductive circuit pattern is present on one face thereof and the wiper plate 45 and rotatable limit switch board are mounted in line in the instrument and in contact with each other concentrically about the drive shaft. As the drive shaft rotates clockwise or counterclockwise, the circuit pattern on the rotatable limit switch board creates particular circuit paths by connecting specific spring finger contacts during the rotational action. The purpose of these specific circuit paths on the rotatable limit switch board allows the stylet/cannula assembly to stop at prescribed positions.

The instrument is also provided with a toggle assembly which includes a stationary wiper plate 28, toggle board 34 and toggle plate 40. The stationary wiper plate is very similar to the stationary limit switch wiper plate 45 in the limit switch assembly and is also provided with six spring finger contacts 29 which are an electrical contact with the actuation buttons and other circuit components. Toggle board 34 has electrically conductive circuit pattern 30 deposited on one face. Wiper plate 28 and toggle board 34 are mounted in line and in contact with each other concentrically about the drive shaft 25. As the drive shaft rotates either clockwise or counterclockwise, key 27 on shaft 25 contacts protrusion 37 on the toggle board. When the key and protrusion meet the toggle board is forced to rotate a slight distance in clockwise or counterclockwise direction and the circuit pattern on the toggle board creates a particular circuit path by being in contact with specific spring fingers 29. The amount of rotation of the toggle board is controlled by pin 38 riding in V-shaped opening 43. The purpose of the specific circuit paths of the toggle board is to allow the stylet/cannula assembly to travel in prescribed directions of motion via depression of the retract button 80. This particular construction allows the retract button 80 to serve as a dual function switch in the retraction phase of the biopsy instrument. After the forward motion of the stylet/cannula assembly is completed, retract button 80 can be pressed and the stylet of the stylet/cannula assembly moves back or retracts resulting from approximately one-half a revolution of the special function cam. The limit switch assembly stops the rotation at approximately the mid-point of reverse travel and the toggle board is mechanically rotated as previously described. The shift in the position of the toggle board 34 changes the electrical circuitry to allow a second actuation of the retract button which continues the cam rotation until the limit switch assembly stops rotation at the end of travel and the cannula is fully retracted.

FIGS. 10A-10G illustrate schematically the basic circuitry involved in various actions of the biopsy instrument. In these figures, the circuitry and activity of the toggle assembly is shown generally at 90, and the circuitry and activity of the limit switch assembly is shown generally at 100. Connectors 31 of the stationary wiper plate 28 of the toggle assembly are designated "+", "B", "C", "−", "D" and "A". Connectors 48 of the limit switch wiper plate 45 are designated "K", "G", "H", "E", "I", and "J". In the limit switch assembly schematic 100, the arm limit switch is designated 102 and the sample limit switch is designated 104. In the toggle assembly schematic 90, the positions of the rotatable toggle board 34 are designated either 92 or 94. Closing the arm limit switch 102 initiates the sequential, linear forward motion of both the stylet and cannula. The arm limit switch 102 thus controls the sequential forward movement of the stylet/cannula assembly. The sample limit switch 104 controls the retraction of the cannula. The path of current flow of all FIGS. 10A-10G is shown with bold lines.

Figure 10A:
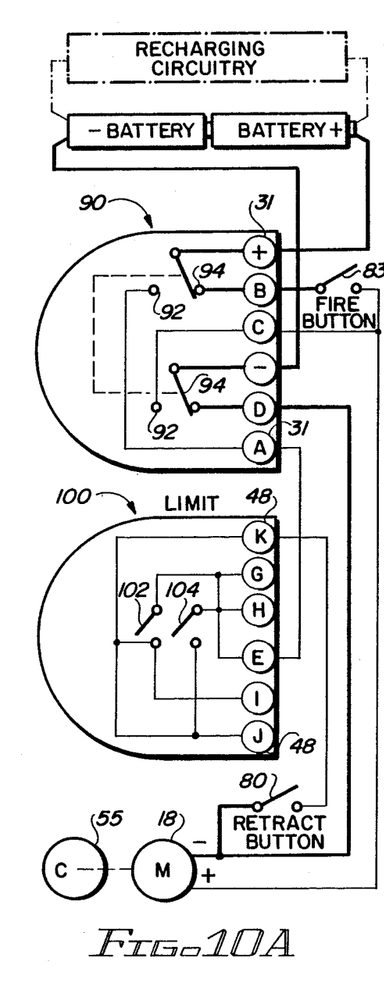
FIGS. 10A-10G are schematic drawings showing the electrical circuitry involved in the various actions of the biopsy instrument.

FIG. 10A illustrates a ready to fire situation; that is, both the stylet and cannula are fully retracted. The toggle board 34 has rotated with an imaginary point on the shaft 25 or cam 55 being at 0 degrees. As shown FIG. 10A, the position of the toggle board is at 94 which allows current to flow only to fire button 83. Both the arm limit switch 102 and the sample limit switch 104 are open and the retract button is therefore not in the circuit and even if depressed, no action would occur.

Figure 10B:
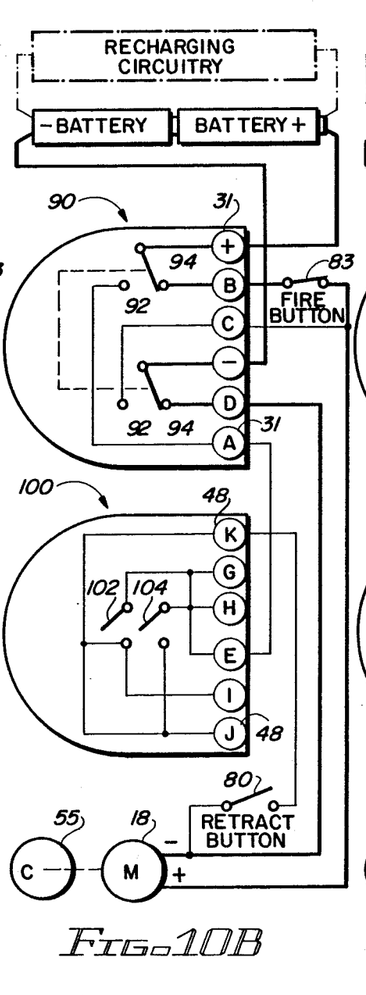

FIG. 10B illustrates what happens when the fire button 83 is depressed. Depression of the fire button sends current to the motor "M" causing rotation of the cam "C" 55 and forward movement of the stylet and cannula. As shown in the limit switch assembly 100 of FIG. 10B, both the arm limit switch 102 and sample limit switch 104 are open and no current is flowing through the limit switch assembly.

Figure 10C:
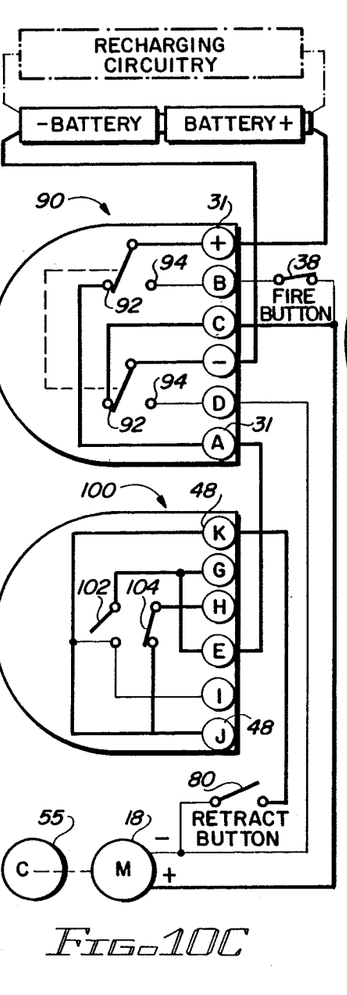

FIG. 10C illustrates the situation at the end of the fire cycle shown in FIG. 10B. At this point, shaft 25 and cam 55 have rotated approximately 320 degrees from an initial 0 degree position and each of the stylet and cannula have moved sequentially to a fully extended position. Key 27 on shaft 25 has made contact with protrusion 37 of toggle board 34 to rotate toggle board 34 which in turn causes the toggle switches to move from position 94 to position 92. This movement of the toggle switches results in a break in the circuit path to motor M. In the limit switch assembly 100, the arm limit switch 102 is open, and the sample limit switch 104 is closed. Both the stylet and cannula are forward.

Figure 10D:
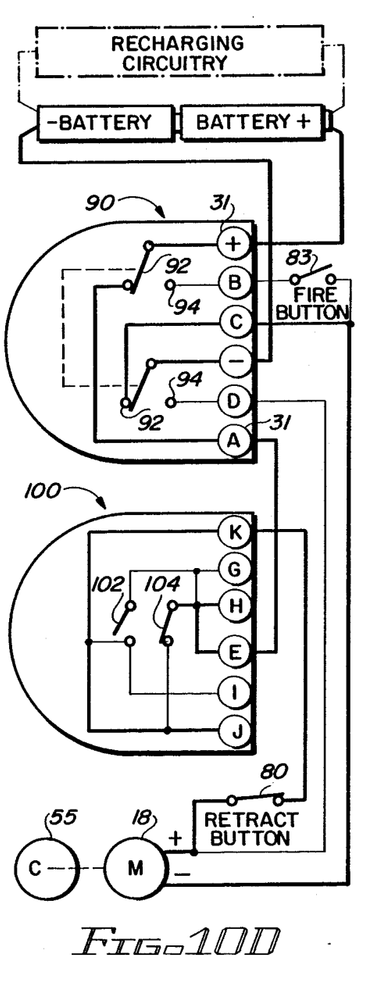

In FIG. 10D, the circuit at fire button 83 is now open and the toggle switches of the rotatable toggle board 34 are at the position designated 92, as they were at the end of the fire cycle shown in FIG. 10C. The toggle board in this position allows current to flow to the retract button 80 via the limit switch assembly circuit. As shown in the limit switch assembly circuit 100, the sample limit switch 104 is closed and the arm limit switch 102 is open. Thus, depression of retract button 80 causes the motor M to reverse, causing rotation of the cam to reverse, resulting in retraction of the cannula.

Figure 10E:
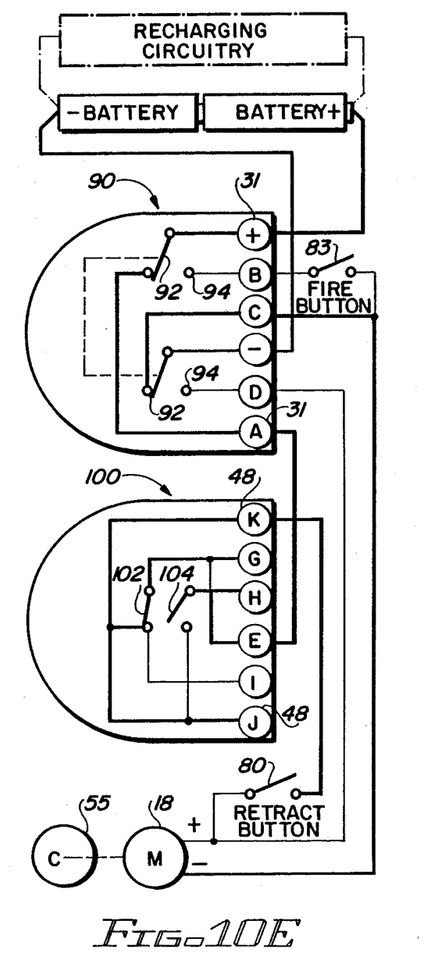

In FIG. 10E, the toggle switches of the toggle board are at position 92 and in this position actuation of the fire button would have no effect. In the limit switch assembly circuit 100, arm limit switch 102 is closed and the sample limit switch is open. The retract button circuit 80 is open preventing any further cam motion. In this situation, the cannula is back and the stylet is forward.

Figure 10F:
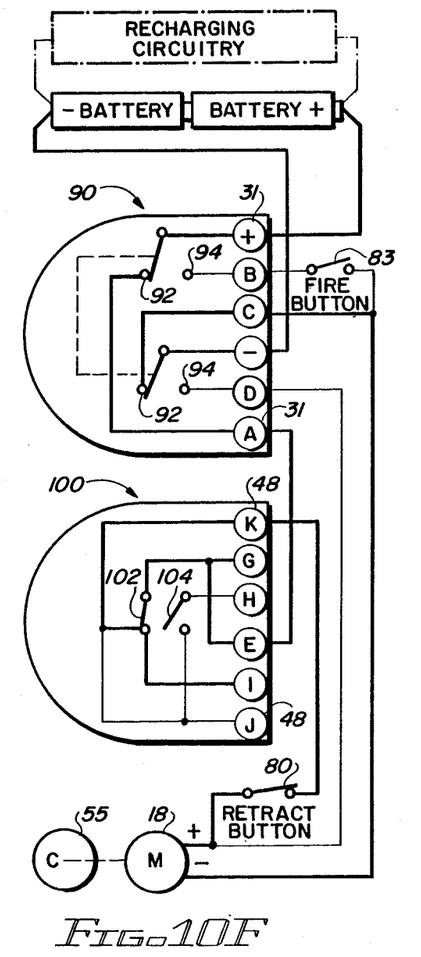

FIG. 10F, shows the activity upon a second depression of the retract button 80. In the toggle assembly 90, the toggle board switches are in the position designated 92 which allows current to flow to the retract button via the limit switch assembly circuit 100. The arm limit switch 102 is closed. When the retract button is depressed motor M operates retracting the stylet and thus both the stylet and cannula are in a ready to fire position.

Figure 10G:
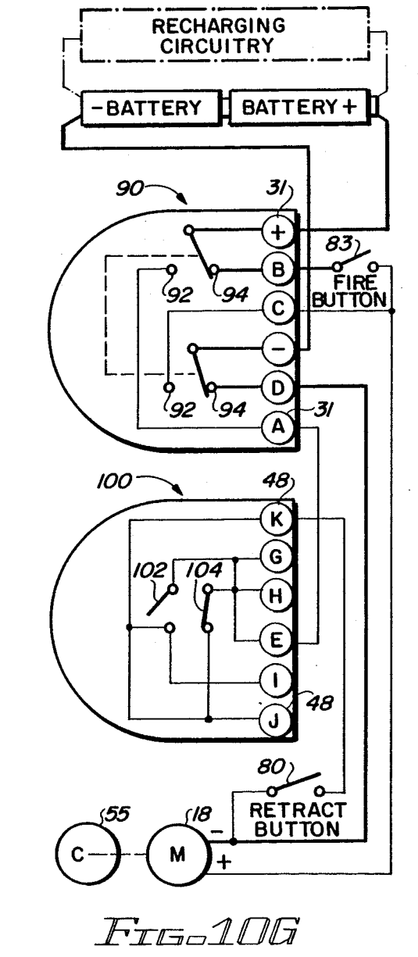
Figures 11A, 12:
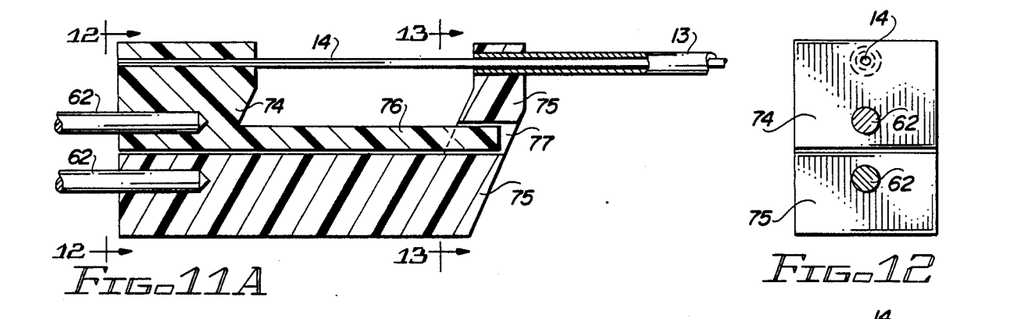
FIGS. 11A and 11B are part side sectional views of the biopsy instrument showing the action and construction of the cannula and stylet blocks.
FIG. 12 is a section taken on the line 12—12 of FIG. 11A.
Figure 11B:
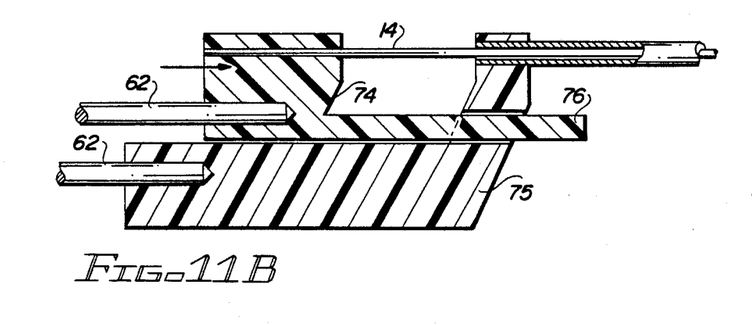

FIG. 10G illustrates the situation at the end of the retraction of both the stylet and cannula. At the end of the retraction cycle, the drive shaft key moves the toggle board to a 20 degree rotation point. In the limit switch assembly 100, the arm limit switch 102 is open and the sample limit switch 104 is closed. Thus the retract button is not in the circuit at this point, and no action will occur even if depressed.

Figure 14A:
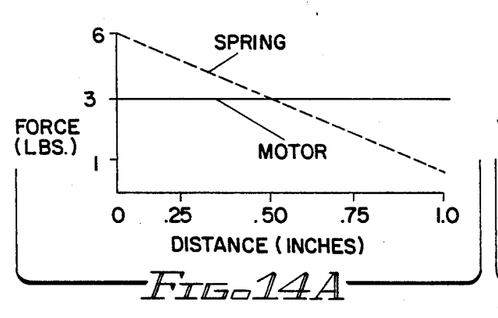
FIGS. 14A and 14B are graphs comparing the force and velocity delivered by the tissue penetrating and severing means of a typical spring powered biopsy gun and the instrument of the present invention.
Figure 14B:
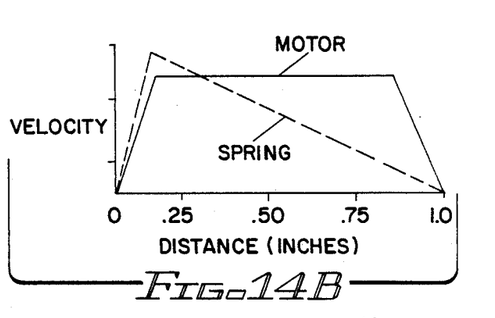

One of the features of the instrument of this invention is its ability to deliver a substantially constant force and velocity to the tissue penetrating and severing means, that is the stylet and cannula, thereby obtaining a higher quality tissue sample. This is graphically illustrated in FIGS. 14A and 14B where the force and velocity of a typical spring powered instrument (indicated by a dashed line) is compared with the biopsy instrument of this invention (indicated by a solid line). Assuming that the stylet and cannula travel a distance of about 1 inch from a retracted to a fully extended position, as shown in FIG. 14A it will be seen that the instrument of this invention delivers a virtually constant force to the stylet and cannula from a retracted to fully extended position. On the other hand, the spring powered instrument, although initially delivering a considerably greater force, this force diminishes very rapidly due to tissue resistance and spring characteristics. Substantially the same is true with respect to the velocity of the stylet and cannula of the two instruments. As shown in FIG. 14B, although the initial velocity of each instrument is about the same, the instrument of this invention delivers a constant velocity over almost all of the travel of the stylet and cannula whereas in the spring powered instrument the velocity again diminishes very rapidly throughout the required travel.

What is claimed is:

1. A motor powered instrument for removing a tissue sample from a tissue mass comprising a housing, a tissue penetrating means and severing means disposed at one end of said housing, operating means positioned in said housing and operably connected to said tissue penetrating means and severing means for causing relative linear movement of said tissue penetrating means and said severing means in a sequential manner whereby said tissue penetrating means proceeds by linear movement from a retracted to an extended position followed by linear movement of said tissue severing means from a retracted to an extended position to effect a severing of a portion of said tissue mass, said operating means including motor means and means to convert rotary motion to sequential, reciprocating linear motion of substantially constant force and velocity to said tissue penetrating means and severing means.

2. The instrument of claim 1 wherein said operating means includes cam means comprising a rotatable cylinder having a groove therein and a cam follower means operably connected with said groove and said tissue penetrating means and severing means and drive means operably connecting said motor means to said cam means.

3. The instrument of claim 2 wherein said tissue penetrating means is positioned within said tissue severing means and moveable therein, and wherein said rotatable cylinder is hollow with said groove positioned in the wall thereof and wherein said groove is a continuous groove positioned in a generally spiral manner in said cylinder wall and wherein a portion of said cam follower means engages said groove from within said cylinder.

4. The instrument of claim 3 wherein said continuous groove is formed of a first groove section positioned near one end of said cylinder and substantially parallel thereto and extending around at least a portion of the circumference thereof, a second groove section positioned near the opposite end of said cylinder and substantially parallel thereto and extending around at least a portion of the circumference thereof, and a third groove section connecting said first and second groove sections in a generally diagonal manner.

5. The instrument of claim 4 wherein linear movement of said tissue penetrating means from a retracted to an extended position followed by linear movement of said tissue severing means from a retracted to an extended position is further followed by retraction of said tissue severing means to expose a tissue sample.

6. The instrument of claim 5 wherein a portion of said cam follower means is positioned within said rotatable cylinder in a manner such that rotation of said cylinder in a direction causes said tissue penetrating means to proceed by linear movement from a retracted to an extended position followed by linear movement of said tissue severing means from a retracted to an extended position and wherein rotation of aid cylinder in an opposite direction causes said tissue severing means to proceed by linear movement from an extended to a retracted position.

7. The instrument of claim 6 wherein further rotation of said cylinder in said opposite direction causes said tissue penetrating means to proceed by linear movement from an extended to a retracted position.

8. The instrument of claim 7 wherein said cam follower means include drive rods operably connecting each of said tissue penetrating means and severing means with an end of each of said rods having a cam follower which is positioned in said groove.

9. The instrument of claim 8 wherein mounting means are provided operably connecting an end of each said drive rods with an end of each of said tissue penetrating means and severing means.

10. The instrument of claim 9 wherein said mounting means are mounting blocks positioned within guide means to provide proper alignment of said tissue penetrating means and severing means with said cam follower means and said rotatable cylinder.

11. The instrument of claim 10 wherein said mounting blocks are positioned immediately adjacent each other and slideably mounted within said guide means.

12. The instrument of claim 2 wherein said operating means further includes means for controlling the sequential linear movement of said tissue penetrating means and severing means, said control means functioning to control the rotation of said cylinder in a clockwise or counterclockwise direction and to stop the rotation of said cylinder at prescribed locations.

13. The instrument of claim 12 wherein said control means comprises a toggle assembly and a limit switch assembly, said toggle assembly functioning to control the rotation of said cylinder and thereby control the linear movement of said tissue penetrating means and severing means in a prescribed direction, said limit switch assembly functioning to stop the rotation of said cylinder and thereby stop the linear movement of said tissue penetrating means and severing means at prescribed locations, and means to actuate said control means.

14. The instrument of claim 13 wherein said toggle assembly comprises a plate having electrically conductive contact means on a side thereof, a toggle board with a side thereof provided with electrically conductive circuit paths in contact with the contact means of said plate, and means for adjusting the relative positions of said toggle board and said plate to create different electrical circuits, and wherein said limit switch assembly comprises a plate having electrically conductive contact means on a face thereof and a rotatable limit switch board with a side thereof provided with electrically conductive circuit paths in contact with the contact means of said plate whereby rotation of said limit switch board creates different electrically conductive circuits.

15. The instrument of claim 14 wherein said limit switch assembly stops the rotation of said cylinder and thereby the linear movement of said tissue penetrating means and severing means at locations where both said tissue penetrating means and severing means are in an extended position, where the tissue severing means are retracted and where both the tissue penetrating means and severing means are retracted.

16. The instrument of claim 15 wherein said means for adjusting the relative positions of said toggle board and said plate is provided on said drive means whereby said toggle board is caused to rotate slightly either clockwise or counterclockwise.

17. The instrument of claim 15, wherein said actuation means comprises two actuation means whereby actuation of one of said means causes sequential linear movement of said tissue penetrating means and severing means from a retracted to an extended position and wherein initial actuation of the other of said means causes linear movement of said tissue severing means from an extended to a retracted position.

18. The instrument of claim 9 wherein an additional actuation of said other means causes linear movement of said tissue penetrating means from an extended to a retracted position.

19. A motor powered instrument for removing a tissue sample from a tissue mass comprising a housing, tissue penetrating means and severing means disposed at one end of said housing, said tissue penetrating means positioned within said tissue severing means and moveable therein, operating means positioned in said housing and operably connected to said tissue penetrating means and severing means for causing relative linear movement of said tissue penetrating means and said severing means in a sequential manner whereby said tissue penetrating means proceed by linear movement from a retracted to an extended position followed by linear movement of said tissue severing means from a retracted to an extended position to effect a severing of a portion of said tissue mass, followed by retraction of said tissue severing means to expose a tissue sample, and followed further by retraction of said tissue penetrating means, said operating means comprising a motor, cam means to convert rotary motion to sequential, reciprocating, linear motion of substantially constant force and velocity in said tissue penetrating means and severing means, said cam means comprising a rotatable hollow cylinder having a continuous groove positioned in a wall thereof, said continuous groove being formed of a first groove section positioned near one end of said cylinder and substantially parallel thereto and extending around at least a portion of the circumference thereof, a second groove section positioned near the opposite end of said cylinder and substantially parallel thereto and extending around at least a portion of the circumference thereof, and a third groove section connecting said first and second sections in a generally diagonal manner, and cam follower means operably connected to said groove and said tissue penetrating means and severing means, and guide means to maintain alignment of said cam follower means and said tissue penetrating means and severing means, drive means operably connecting said motor to said cam means, said drive means including a gear assembly connected to said motor, a drive shaft operably connected to said gear assembly and said rotatable hollow cylinder, and means for controlling the sequential linear movement of said tissue penetrating means and severing means, said control mean comprising a toggle assembly and a limit switch assembly, said toggle assembly functioning to control the rotation of said cylinder and thereby control the linear movement of said tissue penetrating means and severing means in a prescribed directions, said limit switch assembly functioning to stop the rotation of said cylinder and thereby stop the linear movement of said tissue penetrating means and severing means at prescribed locations, said toggle assembly comprising a plate having electrically conductive contact means on a side thereof, a toggle board with a side thereof provided with electrically conductive circuit paths in contact with the contact means of said plate, said toggle board being rotatable in a clockwise or counterclockwise direction so as to adjust the relative position of said toggle board with respect to said plate to create different electrical circuits, and wherein said limit switch assembly comprises a plate having electrically conductive contact means on a face thereof and a limit switch board rotatable with said drive shaft with a side thereof provided with electrically conductive circuit paths in contact with the contact means of said plate whereby rotation of said limit switch board creates different electrically conductive circuits, and two actuation means to actuate said control means whereby actuation of one of said means causes sequential linear movement of said tissue penetrating means and severing means from a retracted to an extended position and wherein initial actuation of the other of said means causes linear movement of said tissue severing means from an extended to a retracted position and subsequent actuation of said other means causes linear movement of said tissue penetrating means from an extended to a retracted position.

20. The instrument of claim 19 wherein said tissue penetrating means is a stylet having a notch in the tissue penetrating end thereof and said tissue severing means is a cannula, said motor is DC powered, said gear assembly includes a central gear, a planetary gear assembly and an annulus gear, and wherein said drive shaft is provided with means in contact with means on said toggle board whereby rotation of said drive shaft either clockwise or counterclockwise results in rotation of said toggle board in a clockwise or counterclockwise direction.

* * * * *

UNITED STATES PATENT AND TRADEMARK OFFICE
CERTIFICATE OF CORRECTION

PATENT NO.　:　4,940,061

DATED　　　:　July 10, 1990

INVENTOR(S):　Richard A. Terwilliger et al.

It is certified that error appears in the above-identified patent and that said Letters Patent is hereby corrected as shown below:

On the title page:
The Assignee should be listed as: Vance Products Incorporated d/b/a Cook Urological Incorporated.

At column 7, line 57, "separating guide 65" should read --separating guide 64--.

At column 11, line 13, "and a cam" should read --and cam--.

At column 11, line 50, "rotation of aid cylinder" should read --rotation of said cylinder--.

At column 14, line 2, "prescribed directions" should read --prescribed direction--.

Signed and Sealed this

Thirtieth Day of June, 1992

Attest:

DOUGLAS B. COMER

*Attesting Officer*　　　*Acting Commissioner of Patents and Trademarks*